Figure 1:
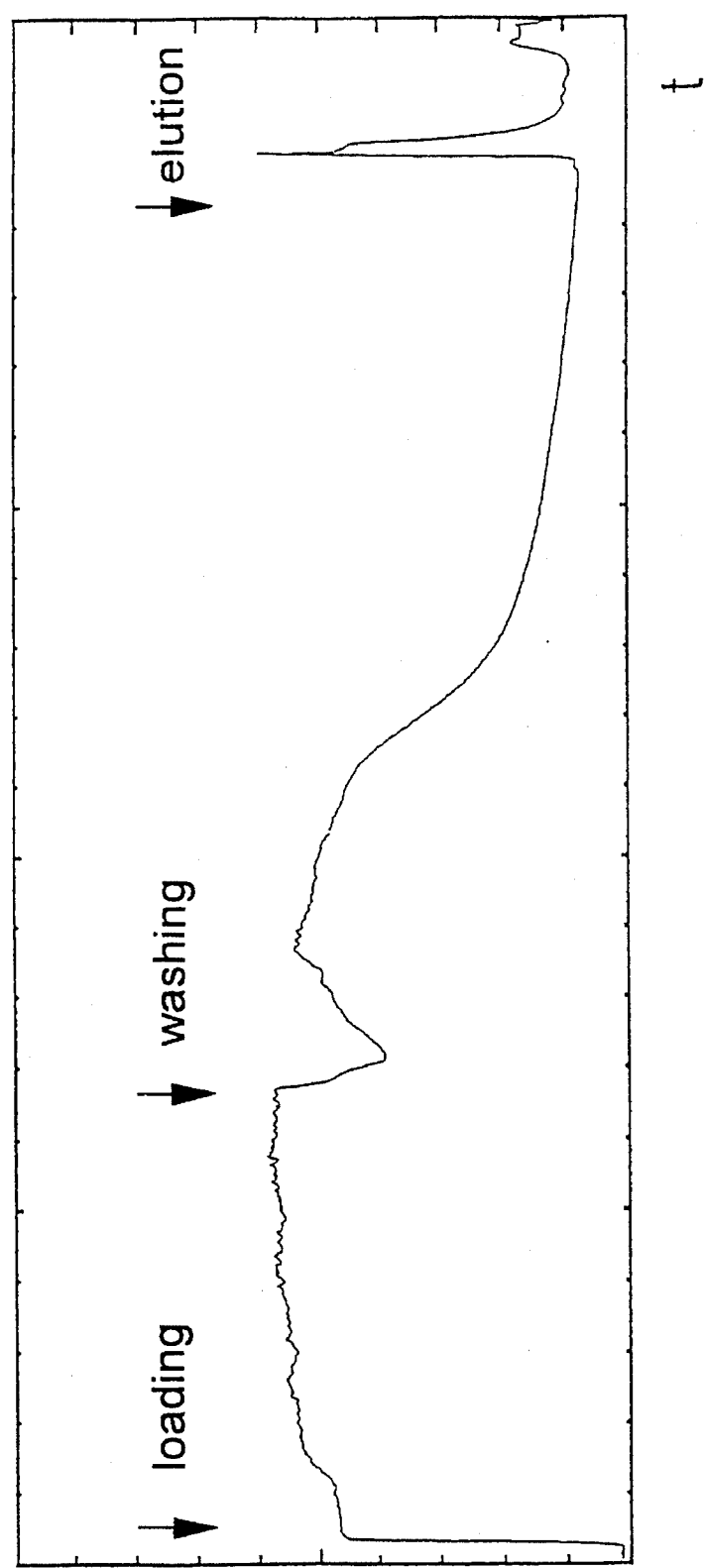

United States Patent [19]

Hodler et al.

[11] Patent Number: 5,593,675
[45] Date of Patent: Jan. 14, 1997

[54] METHOD OF PRODUCING AN ANTI-D IMMUNOGLOBULIN CONCENTRATE AND A PHARMACEUTICAL PREPARATION

[75] Inventors: Gerhard Hodler, Worb; Peter Lerch, Bern; Martin Stucki, Laupen, all of Switzerland

[73] Assignee: Rotkreuzstiftung Zentrallaboratorium Blutspendedienst, Bern, Switzerland

[21] Appl. No.: 360,334

[22] Filed: Dec. 21, 1994

[30] Foreign Application Priority Data

Dec. 27, 1993 [CH] Switzerland ............ 93810912.1

[51] Int. Cl.$^6$ .................. A61K 39/395; C07K 16/46; C07K 1/14
[52] U.S. Cl. .................. 424/130.1; 530/413; 530/387.1; 530/389.1; 530/389.6
[58] Field of Search ..................... 530/413, 387.1, 530/389.1, 389.6; 424/130.1

[56] References Cited

U.S. PATENT DOCUMENTS

| | | | |
|---|---|---|---|
| 3,869,436 | 3/1975 | Falksveden | 260/112 B |
| 4,434,093 | 2/1984 | Zolton et al. | 260/112 |
| 4,877,866 | 10/1989 | Rudnick et al. | 530/387 |
| 5,138,034 | 8/1992 | Uemura et al. | 530/413 |

FOREIGN PATENT DOCUMENTS

| | | | |
|---|---|---|---|
| 085747A2 | 8/1983 | European Pat. Off. | A61K 39/395 |
| 440483A2 | 8/1991 | European Pat. Off. | C07K 3/28 |
| WO89/05157 | 6/1989 | WIPO | A61K 39/395 |

OTHER PUBLICATIONS

Friesen et al., "Column Ion–Exchange Preparation and Characterization of an Rh Immune Globulin (WinRho) for Intravenous Use," *Journal of Applied Biochemistry* 3:164–175, 1981.
Horowitz et al., "Preparation and Characterization of S/D–FFP," A Virus Sterlized Fresh Frozen Plasma, *Thrombosis and Haemostasis* 65(6):1163, Abstract #1681, 1991.

Reynolds, James E. F. (ed.), *Martindale, The Extra Pharmacopoeia*, The Pharmaceutical Press, London, 1989, pp. 811–812, 1170–1171.
Le Van Kim et al., "Molecular cloning and primary structure of the human blood group RhD polypeptide," *Proc. Natl. Acad. Sci. U.S.A.* 89:10925–10929, 1992.
Morell et al., "In Vivo Behaviour of Gamma Globulin Preparations," *Vox Sang* 38:272–238, 1980.
Curling, J. M. (ed.), *Separation of Plasma Proteins*, Pharmacia Fine Chemicals AB, Uppsala, Sweden, 1983.
Kistler and Nitschmann, "Large Scale Production of Human Plasma Fractions. Eight Years Experience with the Alcohol Fractionation Procedure of Nitschmann, Kistler and Lergier," *Vox Sang* 7:414–424, 1962.
Cohn et al., "Preparation and Properties of Serum and Plasma Proteins. IV. A System for the Separation into Fractions of the Protein and Lipoprotein Components of Biological Tissues and Fluids," *Journal of the American Chemical Society* 68:459–475, 1946.

*Primary Examiner*—Lila Feisee
*Attorney, Agent, or Firm*—Seed and Berry LLP

[57] ABSTRACT

An anti-D immunoglobulin G-preparation is produced in high-yield from human plasma containing anti-D IgG, or a plasma fraction containing an anti-D IgG, in which (A) the plasma, or the plasma fraction, with a pH in the range of pH 3.5 to 6.5 and a conductivity value in the range of 2 to 4 mS/cm, is subjected to ion exchange chromatography with an adsorbent which has carboxymethyl groups as functional groups, the anti-D IgG being bound to the adsorbent, (B) the adsorbent with the bound anti-D IgG is first rinsed with a wash solution at a pH in the range of 5 to 8 and a conductivity value in the range of 2 to 4 mS/cm, and the anti-D IgG is subsequently eluted, and further (C) the eluted anti-D IgG at a pH in the range of 6 to 8 and a conductivity value in the range of 2 to 4 mS/cm is treated with an alkaline adsorbent with ion-exchange characteristics in order to bind undesired components, and finally, the anti-D IgG is concentrated. The non-infectious anti-D concentrate thus obtained possesses a high specific activity of more than 1% anti-D IgG per gram of total IgG.

20 Claims, 1 Drawing Sheet

METHOD OF PRODUCING AN ANTI-D IMMUNOGLOBULIN CONCENTRATE AND A PHARMACEUTICAL PREPARATION

This invention relates to a method of producing a new concentrate of anti-D (anti-rhesus) immunoglobulin G (anti-D IgG) as well as a pharmaceutical preparation which contains such a concentrate as its active component.

Morbus haemolyticus neonatorum is the general designation for the haemolytic anaemia of fetuses and newborn babies caused by antibodies of the mother. These antibodies are directed against antigens on the surface of the fetal erythrocytes. Involved thereby are either antigens of the rhesus, ABO or other blood group systems.

The most important antigens of the rhesus blood groups are D, the clearly less immunogenic antithetical antigens C, c and E, e as well as $D^u$; in addition over 40 further rhesus antigens are known. Of clinical significance for rhesus incompatibility is above all the rhesus antigen D (RhD; $Rh_0$), a membrane protein of the erythrocytes which was cloned recently and its primary structure described (Le Van Kim et al. PNAS USA, 89, 10925, 1992). The D-antigen can be found in approximately 85% of Caucasians in Europe. Individuals having the D-antigen are called Rh-positive. Individuals lacking the D-antigen are called Rh-negative. Antibodies of the specifity anti-D are the most common irregular rhesus antibodies and arise above all during rhesus-incompatible pregnancies and following transfusion of rhesus-incompatible blood. Anti-D antibodies belong predominantly to the IgG subclasses 1 and 3 (IgG1 and IgG3).

Up until now no unfailing, effective causal treatment of rhesus-sensitisized pregnant women has been known. Since desensitization is likewise not possible, prophylaxis of rhesus sensitization with immunoglobulin anti-D is of decisive importance for Rh-negative women of child-bearing age.

Without treatment, up to 17% of the primigravidae with the rhesus constellation (mother Rh-negative, child Rh-positive) would become sensitized to the rhesus antigen in the course of pregnancy or during delivery.

Anti-D preparations have been used successfully for over 30 years to prevent the rhesus sensitization of Rh-negative, or respectively $D^u$-positive, women to the rhesus factor D, or respectively $D^u$, and thus to prevent anti-D-related diseases among newborns, namely rhesus-erythroblastose in all its forms.

The risk of rhesus sensitization increases with the amount of inflow of fetal Rh-positive erythrocytes. The treatment dosage recommended by the WHO of 200 μg anti-D IgG as postpartum prophylaxis suffices to neutralize up to 10 ml of fetal erythrocytes (corresponding to approximately 20 ml of fetal blood), and thus protects against an Rh sensitization in approximately 90% of the cases, even with greater amounts of inflow; consequently sensitization to the rhesus antigen is still to be expected in only 1–2% of all primagravidae with rhesus constellation. Through additional routine rhesus prophylaxis during pregnancy (antepartum prophylaxis), the remaining risk of sensitization can be reduced again to 0.1–0.2% of all primagravidae with rhesus constellation.

In addition anti-D is also used after mistransfusions of Rh-positive blood to Rh-negative recipients; the dosage is to be adapted thereby to the amount of inflow of Rh-positive erythrocytes.

Use of anti-D immunoglobulin in treatment of idiopathic thrombocytopenic purpura (ITP) has been under discussion for some years.

The pharmacokinetics of intramuscular and intravenous injected IgG in the organism show clearly that intravenous application is to be preferred by all means. With intramuscular injection, a delay in maximum activity and losses in effectiveness must be expected, owing to the slow absorption from the muscle depot and local proteolysis. The maximum IgG plasma concentration is not reached in healthy test subjects until four days after injection, in bedridden test subjects not until six days after injection. Moreover, the maximum IgG plasma concentration in healthy test subjects is only about 30% of the injected dosage, in bedridden test subjects only 20%.

By comparison, intravenous application brings considerable advantages. Only with this kind of application does the entire administered dosage take effect regardless of physical activity; the IgG plasma level sinks in the course of 5 days, practically independently of bodily activity, to about 35–40% of the administered dosage, and therefore reaches only on the fifth day values comparable to the maximal plasma concentration achieved following intramuscular injection. (Morell, A. et al. Vox Sang. 38, 272, 1980).

For producing immunoglobulin preparations on an industrial scale, various fractionation processes are used today:

Cold ethanol precipitation methods, for example according to Cohn, or a modified procedure based on Cohn, are suitable above all for processing plasma quantities of over 500 l per week. Through special treatment, for example with pepsin at pH 4, immunoglobulins isolated in this way can be made to be intravenously well tolerated. Other precipitation methods are based on the specific precipitation of immunoglobulin by ammonium sulfate, sodium sulfate, polyethylene glycol, caprylic acid or rivanol (for an overview, see Curling, J. M., Separation of Plasma Proteins, J. M. Curling, ed., 1983, Pharmacia, Uppsala, Sweden).

A method of isolating immunoglobulin by batch adsorption on ion exchangers was first described as early as 1964 (Baumstark, J. S. et al. Arch. Biochem. Biophys., 108, 514, 1964). In the following years a number of column procedures have also been developed (CH-A-572745; U.S. Pat. No. 3,869,436; EP-A-0 085 747), and used for, among other things, the fractionation of anti-D immunoglobulin (Friesen, A. D. et al. J. Appl. Biochem. 3, 164, 1981).

Achieved with all the procedures described is a high yield of whole IgG having a high level of purity and unchanged IgG subclass distribution, but no specific concentration of certain IgG subclasses or specific IgG molecules, such as, for example, anti-D IgG.

Most of the anti-D hyperimmunoglobulin preparations are suitable for intramuscular application only. Worldwide there are only a few intravenously well tolerated preparations on the market. One such preparation is the immunoglobulin anti-D SRK of the present applicant, which is produced according to the fractionation method of Kistler and Nitschmann (Kistler, P. and Nitschmann, H. Vox Sang, 7, 414, 1962) and which is made intravenously well tolerated by means of a mild pepsin treatment at pH 4. Since the yield of specific anti-D antibodies is very low with this type of fractionation method, and at the same time anti-D hyperimmune plasma is rare, there has been a need for a new method which, unlike the methods described, would result, also with low-titer anti-D plasma pools, in a pure IgG preparation, having high yield and high specific anti-D activity.

Thus the object of the present invention is to provide a method of producing a pure anti-D concentrate in which the anti-D immunoglobulin of the IgG subclasses 1 and 3 are specifically concentrated. It was discovered that this can be done in a surprisingly simple way, eliminating at the same time over 85% of the unspecific IgG and nearly all of the undesired other plasma components, in that blood plasma, or fractions containing immunoglobulin obtained therefrom, of specially chosen and specially immunized blood donors, having a titer of preferably more than 30 µg/ml anti-D IgG, is subjected to cation exchange chromatography under conditions according to the invention. The anti-D concentrate obtained with high yield has in addition an increased specific activity (gram of anti-D IgG per gram of total IgG) and can be purified further through additional treatments with other ion exchangers or aluminum hydroxide gel individually or in suitable combination.

Another object of this invention is to provide an anti-D preparation which contains IgA only in traces, which is intravenously well tolerated, and which, with the addition of suitable stabilizers, alternatively lyophilized or preferably in solution, can be stored for several months without loss of activity. It was found that the pure anti-D concentrate obtained by means of the proposed method according to the invention fulfils these requirements, i.e. that it has, among other things, a specific activity which has never been achieved before, is intravenously well tolerated and has an extremely low IgA content. In addition, the anti-D concentrate has an abnormal IgG subclass distribution, in that by means of the method the IgG subclasses 1 and 3 are greatly enriched, the subclasses 2 and 4 however greatly reduced.

The subject matter of the present invention is therefore a method for producing an anti-D immunoglobulin G preparation with a specific activity of more than 1% anti-D IgG per gram of total IgG, from human plasma, wherein plasma from Rh-negative blood of donors sensitized to rhesus factor D, or a plasma fraction containing anti-D IgG, A) with a pH in the range of pH 3.5 to 6.5 and a conductivity value in the range of 2 to 4 mS/cm, is subjected to an ion exchange chromatography with an adsorbent which has carboxymethyl groups as functional groups, the anti-D IgG being bound to the adsorbent, B) the adsorbent with the bound anti-D IgG is first rinsed with a wash solution at a pH in the range of 5 to 8 and a conductivity value in the range of 2 to 4 mS/cm, and the anti-D IgG is subsequently eluted, and further C) the eluted anti-D IgG at a pH in the range of 6 to 8 and a conductivity value in the range of 2 to 4 mS/cm is treated with an alkaline adsorbant with ion-exchange characteristics in order to bind undesired components, and finally the anti-D IgG is concentrated.

With the method according to the invention, immunoglobulin can be obtained directly from human plasma. The starting material is the plasma from Rh-negative donors sensitized to the rhesus factor D. The individual donation obtained through plasmapheresis is preferably frozen and carefully thawed at 0°–4° C. before fractionation, and pooled. The plasma pool should contain more than 10 µg anti-D IgG per ml, preferably more than 30 µg anti-D IgG per ml. The plasma fraction used for the cation exchange chromatography can be purified preliminarily using any known method, such as, for example, by separation of the cryoglobulins or by fractionated precipitation by means of ethanol (Cohn, E. J. et al. J. Am. Chem. Soc. 68, 459, 1946; Kistler and Nitschmann, H. Vox Sang. 7, 414, 1962), by other precipitation methods, such as precipitation of the immunoglobulins by ammonium sulfate, sodium sulfate, polyethylene glycol, caprylic acid or rivanol, or by a chromatographic method or a combination of such methods. Prior to the cation exchange chromatography according to the invention, the cryoglobulin-free plasma or the plasma fraction containing immunoglobulin dissolved in the equilibration buffer is preferably filtered, and to inactivate hidden viruses it is treated with a biocompatible, organic solvent such as, for example, tri(n-butyl) phosphate and a detergent, such as, for example, O-[4-(1,1,3,3-tetramethylbutyl)-phenyl]-deca-(oxyethylene) (Triton$^R$ X-100) based on the method described by Horowitz (Thrombosis and Haemostasis 65, 1163, 1991). The mixture of plasma, solvent, and detergent is then incubated at 37° C. A phase separation takes place thereby. The clear lower phase is separated, diluted, filtered, and adjusted to the equilibration conditions of the cation exchange chromatography, the temperature for the subsequent steps being, as a rule, above 10° C. and preferably 20°–25° C. In a first main purification step, the anti-D IgG from the pretreated product is bound to a weakly acidic ion exchange gel with preferably carboxymethyl (CM) as functional group. Over 98% of foreign proteins are thereby washed away; the solvent and detergents used for virus inactivation are likewise removed here. The anti-D IgG of the IgG subclasses 1 and 3 specifically concentrated by this process step is eluted by the ion exchange gel by increasing conductivity to preferably over 10 mS/cm. The eluate is a pure IgG fraction; it contains less than 15% of the total IgG fraction and has a changed IgG subclass spectrum: IgG1 and IgG3 are strongly concentrated, IgG2 and IgG4 are greatly reduced. This anti-D IgG fraction is then purified further by treatment with a second, weakly alkaline ion exchange gel, with preferably diethylaminoethyl (DEAE) as functional group, anti-D IgG not being bound to the ion exchangers under the selected conditions. To increase concentration, the purified anti-D IgG fraction is preferably bound a second time to a CM ion exchange gel and is eluted as concentrated as possible under suitable conditions, and is manufactured into the final product. For achieving the conditions according to the invention it is not of significance whether the anti-D IgG fraction is eluted by increasing the ionic concentration, or by pH shift or by a buffer changed in composition. To reduce the concentration of further undesired components, such as, for example, proteases, the immunoglobulin solution can be treated additionally with an adsorbent, such as, for example, aluminum hydroxide gel, during any stage of the process. The solvent-detergent treatment can be replaced or supplemented by any known virus inactivation/removal step, for example, heat treatment, such as pasteurization, for example, or nanofiltration.

An anti-D IgG produced according to the invention is fluidly stable. It is furthermore intravenously well tolerated, has an IgA content of less than 5 µg/ml and has an IgG content of 1–10 mg/ml. The pH is approximately 5.2. The preparation contains preferably up to 25 mM of phosphate, up to 200 mM NaCl and up to 100 mg/ml human albumin, and alternatively 250–300 mM of an amino acid, such as, for example, glycine, or up to 100 mg/ml of a disaccharide, such as, for example, sucrose, or 50 mg/ml of a monosaccharid, such as, for example, mannitol.

An anti-D IgG which is produced according to the invention can alternatively be lyophilized at a pH of approximately 6.6, with addition of a disaccharide, such as, for example, 100 mg/ml of sucrose, at a dosage of 200 µg anti-D IgG.

FIG. 1 serves to illustrate the present invention, without any limitation being intended thereby. It shows the typical chromatogram of the first cation exchange chromatograph according to Example 1.

The method according to the invention will be explained more closely using the following examples.

EXAMPLE 1

The starting material is plasma of Rh-negative women or Rh-negative men who have been sensitized to rhesus factor D with carefully selected erythrocytes. Every blood donation is tested for the presence of HBs-antigens, HIV antibodies and hepatitis C antibodies and elevated ALAT activity. The plasma obtained through plasmapheresis is individually frozen and carefully thawed at 0°–4° C. prior to fractionation and pooled. The ice-free plasma pool with an anti-D content of 25 µg/ml is centrifuged (1 l/min; 12000 rpm) in a continuous centrifuge (Cepa, Lahr, Germany) at 2°–4° C. The supernatant is filtered through a 1.2 µm filter (Opticap$^R$, Millipore, Bedford Mass., USA). Then virus inactivation takes place based on Horowitz et al. (Thrombosis and Haemostasis 65, 1163, 1991) by means of a solvent-detergent treatment with 1% Triton$^R$ X-100 (Rohm and Haas, Frankfurt, Germany) and 1% tri(n-butyl) phosphate (Merck, Darmstadt, Germany) for 4–4.5 hours at 30° C. The virus-inactivated solution is left standing for 10–18 hours at 37° C. The clear lower phase is separated and filtered through a 0.2 µm filter (Sealkleen NFP 7002, Pall, Dreieich, Germany). 25 l of filtered plasma which has been treated with solvent and detergent is diluted with a 10 mM sodium phosphate buffer to the conductivity of the equilibration buffer (50 mM sodium phosphate buffer, pH 5.5, 3.2 mS/cm), the pH adjusted to 5 5, filtered through a 1.2 µm filter (Opticap$^R$, Millipore, Bedford Mass., USA) and is bound to MacroPrep$^R$ 50 CM (BioRad, Hercules Calif.; USA) in a column with an area of 706 cm$^2$ and a bed height of 7.5 cm, with a flow rate of 150 cm/h, the gel having been previously equilibrated with 50 mM sodium phosphate buffer, pH 5.5. The temperature is kept at 20°–25 ° C. The column is subsequently washed with 40 column-volumes of 25 mM sodium phosphate buffer, pH 7.0, and the IgG fraction containing anti-D is eluted with 25 mM sodium phosphate buffer+0.2M sodium chloride, pH 7.5. The typical chromatogram, as is obtained with this treatment, is shown in the single accompanying Figure. In the diagram the optical density (OD) is recorded at 280 nm over time (t). From this it can be seen that during loading and washing, the majority of the undesired products are separated, while during the elution a major, narrow peak appears which contains the desired anti-D IgG strongly concentrated in an IgG sub-fraction. The specific activity thereby is more than 2% anti-D IgG per g of total IgG. The eluate is diluted with water to a conductivity of 3.3 mS/cm (1 volume of eluate+ approx. 5 volumes of water), the pH adjusted to 7.5 with 0.2M NaOH, and adsorbed in batch method for 2.5 hours with 100 g DEAE-Sephadex$^R$ A50 dry (Pharmacia, Uppsala, Sweden). The DEAE gel has been equilibrated previously with a 25 mM sodium phosphate buffer, pH 7.5. The unbound anti-D IgG fraction is filtered through a polypropylene mesh and the pH adjusted to 5.5. To increase concentration, the DEAE filtrate is bound a second time to MacroPrep$^R$ 50 CM (BioRad, Hercules Calif., USA) in a column with an area of 71 cm$^2$ and a bed height of 12.5 cm, with a flow rate of 230 cm/h, the gel having been previously equilibrated with 50 mM sodium phosphate buffer, pH 5.5. The IgG fraction containing anti-D is eluted with 25 mM sodium phosphate buffer+0.2M sodium chloride, pH 5.5. The CM gels are regenerated with 1N NaOH, and are washed pyrogen-free, and can be used again at least twenty times. The DEAE gel is thrown away after being used just once.

EXAMPLE 2

The starting material is plasma of Rh-negative women or Rh-negative men who have been sensitized to rhesus factor D with carefully selected erythrocytes. Every blood donation is tested for the presence of HBs-antigens, HIV antibodies and hepatitis C antibodies and elevated ALAT activity. The plasma obtained through plasmapheresis is individually frozen and carefully thawed at 0°–4° C. prior to fractionation and pooled. The ice-free plasma pool is centrifuged (1 l/min; 12000 U/min) in a continuous centrifuge (Cepa, Lahr, Germany). The supernatant is filtered through a 1.2 µm filter (Opticap$^R$, Millipore, Bedford Mass., USA). Then virus inactivation takes place based on Horowitz et al. (Thrombosis and Haemostasis 65, 1163, 1991) by means of a solvent-detergent treatment with 1% Triton$^R$ X-100 (Rohm and Haas, Frankfurt, Germany) and 1% tri(n-butyl) phosphate (Merck, Darmstadt, Germany) for 4–4.5 hours at 30° C. The virus-inactivated solution is left standing for 10–18 hours at 37° C. The clear lower phase is separated and filtered through a 0.2 µm filter (Sealkleen NFP 7002, Pall, Dreieich, Germany). 25 l of filtered plasma which has been treated with solvent and detergent is diluted with a 10 mM sodium phosphate buffer to the conductivity of the equilibration buffer (50 mM sodium phosphate buffer, pH 5.5, 3.2 mS/cm), the pH adjusted to 5.5, filtered through a 1.2 µm filter (Opticap$^R$, Millipore, Bedford Mass., USA) and bound to MacroPrep$^R$ 50 CM (BioRad, Hercules Calif.; USA) in a column with an area of 706 cm$^2$ and a bed height of 7.5 cm, with a flow rate of 150 cm/h, the gel having been previously equilibrated with 50 mM sodium phosphate buffer, pH 5.5. The temperature is kept at 20°–25° C. The column is subsequently washed with 40 column-volumes of 25 mM sodium phosphate buffer, pH 7.0, and the IgG fraction containing anti-D is eluted with 25 mM sodium phosphate buffer+0.2M sodium chloride, pH 7.5. At pH 6.6, with the addition of 100 mg/ml sucrose in a dosage of 200 µg anti-D IgG, the eluate is filtered through a 0.2 µm filter (Millidisk$^R$ MCGL-10, Millipore, Bedford Mass., USA) and is subsequently lyophilized.

EXAMPLE 3

5 ml of plasma which has been treated with solvent and detergent is diluted to the conductivity of the equilibration buffer (3.3 mS/cm), and is chromatographed in a column with an area of 2 cm$^2$ and a bed height of 5 cm, with a flow rate of 30 cm/h using DEAE-Sephadex$^R$ A50 (Pharmacia, Uppsala, Sweden). Beforehand the gel has been equilibrated with a 25 mM sodium phosphate buffer, pH 7.5. The temperature is kept at approximately 20°–25° C. For further purification the unbound IgG fraction is adjusted to pH 5.5 with 0.2M HCl and to a conductivity of 3.2 mS/cm and is bound to MacroPrep$^R$ 50 CM (BioRad, Hercules Calif., USA) in a column with an area of 0.8 cm$^2$ and a bed height of 6.5 cm with a flow rate of 230 cm/h, the gel have been equilibrated previously with 50 mM sodium phosphate buffer, pH 5.5. The IgG fraction containing anti-D is eluted with 25 mM sodium phosphate buffer+0.2M sodium chloride, pH 5.5, and is processed into the final product. The DEAE Sephadex$^R$ A50 gel is thrown away after being used once; the MacroPrep$^R$ 50 CM gel is regenerated with 1N NaOH and washed pyrogen-free, and can be used at least twenty times.

EXAMPLE 4

The methods according to Examples 1 to 3 are repeated, but instead of plasma as the starting material a plasma fraction containing immunoglobulin is used which is produced from a corresponding quantity of starting plasma in that fraction I+II+III or fraction II+III according to Cohn (Cohn, E. J. et al. J. Am. Chem. Soc. 68, 459, 1949) or precipitate A or gamma-globulin precipitate according to Kistler and Nitschmann (Kistler, P. and Nitschmann, H. Vox Sang, 7, 414, 1962) are obtained and dissolved in the equilibration buffer to 30 g/l protein, analogous results being obtained.

EXAMPLE 5

The methods according to Examples 1 to 4 are repeated, whereby the IgG fraction containing anti-D is eluted from the MacroPrep$^R$ 50 CM gel (BioRad, Hercules Calif., USA) alternatively with 0.1M glycine+0.5M sodium chloride, pH 9, or generally with pH shift and/or change of the ionic strength and/or other changes in the buffer composition, instead of with 25 mM sodium phosphate buffer+0.2M sodium chloride, pH 7.5, analogous results being obtained.

EXAMPLE 6

The methods according to Examples 1 and 2 are repeated, whereby the MacroPrep$^R$ 50 CM gel (BioRad, Hercules, Calif., USA) is washed alternatively with 10 mM glycine, pH 9, instead of with 25 mM sodium phosphate buffer, pH 7.0, analogous results being obtained.

EXAMPLE 7

The anti-D eluate obtained according to Example 1 is adjusted to the following conditions:

|  | fluid prep. I | fluid prep. II | fluid prep. III | fluid prep. IV |
|---|---|---|---|---|
| Anti-D | 100 µg/ml | 100 µg/ml | 100 µg/ml | 100 µg/ml |
| Glycine | 20.6 mg/ml | 20.6 mg/ml | 20.6 mg/ml | 20.6 mg/ml |
| Albumin | — | 10 mg/ml | 50 mg/ml | 100 mg/ml |
| pH | 5.20 | 5.20 | 5.20 | 5.20 |
| Dose | 2 ml | 2 ml | 2 ml | 2 ml |

|  | fluid prep. V | fluid prep. VI | fluid prep. VII | fluid prep. VIII |
|---|---|---|---|---|
| Anti-D | 100 µg/ml | 100 µg/ml | 100 µg/ml | 100 µg/ml |
| D-mannitol | 50 mg/ml | 50 mg/ml | 50 mg/ml | 50 mg/ml |
| Albumin | — | 10 mg/ml | 50 mg/ml | 100 mg/ml |
| pH | 5.20 | 5.20 | 5.20 | 5.20 |
| Dose | 2 ml | 2 ml | 2 ml | 2 ml | and after filtration through a 0.2 µm filter (Millipak$^R$-20, Millipore, Bedford Mass., USA) is filled under sterile conditions into Hypac syringes ready-for-use (Vetter, Ravensburg, Germany).

EXAMPLE 8

The DEAE filtrate according to Example 1, at a pH of approximately 5.5, is treated with 0.2 g of aluminum hydroxide gel per g protein for 30 minutes at 20°–25° C., and then processed further according to Example 1.

EXAMPLE 9

The methods according to Examples 1 to 6 are repeated, whereby instead of MacroPrep$^R$ 50 CM, one of the following gels with the same functional groups is used alternatively: CM-Spherodex$^R$ (Biosepra, Villeneuve la Garenne, France), CM-Trisacryl$^R$ (Biosepra, Villeneuve la Garenne, France), CM-Sepharose$^R$ FF (Pharmacia, Uppsala, Sweden) or Fractogel$^R$ TSK CM-650 (Merck, Darmstadt, Germany), analogous results being obtained.

EXAMPLE 10

The methods according to Example 1, as well as according to Examples 3 to 6, are repeated, whereby instead of DEAE-Sephadex$^R$ A50, MacroPrep$^R$ DEAE (Biorad, Hercules Calif., USA) is used, analogous results being obtained.

The chromatographic steps in the aforementioned Examples 1 to 6 can be carried out alternatively as batch, column or membrane chromatographies, analogous results being obtained.

We claim:

1. A method of producing an anti-D immunoglobulin G-preparation with a specific activity of more than 2% anti-D IgG per gram total IgG, from human plasma, wherein plasma from rhesus negative blood of rhesus factor D sensitized donors or a plasma fraction containing an anti-D IgG:

(a) with a pH value in the range of pH 3.5 to 6.5 and a conductivity value in the range of 2 to 4 mS/cm is subjected to ion exchange chromatography, with an adsorbent which has carboxymethyl groups as functional groups, the anti-D IgG being bound to the adsorbent, (b) the adsorbent, with the bound anti-D IgG is first rinsed with a wash solution at a pH value in the range of 5 to 8 and a conductivity value in the range of 2 to 4 mS/cm, and the anti-D IgG is subsequently eluted, and then (c) the eluted anti-D IgG with a pH value in the range of 6 to 8 and conductivity value in the range of 2 to 4 mS/cm is treated with an alkaline adsorbent with ion-exchange characteristics in order to bind undesired components, and finally the anti-D IgG is concentrated.

2. The method of claim 1, wherein the anti-D IgG is concentrated in step (c), in-that steps (a) and (a) are repeated at least once.

3. The method of claim 1 or 2, wherein the starting material is plasma, and prior to step (a) said starting material is pretreated with a basic adsorbent with ion-exchange characteristics in order to bind undesired components selected from the group consisting of nonspecific IgG and proteases.

4. The method of claim 1 or 2 wherein the protease content in the plasma or the plasma fraction is reduced through incubation with an adsorbant such as aluminum hydroxide gel.

5. The method of claim 1 or 2, wherein all ion exchange chromatography steps, and if necessary further adsorption steps, are carried out alternatively as batch chromatography, column chromatography or membrane chromatography.

6. The method of claim 1 or 2, wherein the alkaline adsorbent in step (c) has diethylaminoethyl groups as functional groups.

7. The method of claim 1 or 2, wherein the elution in step (b) is carried out with a pH shift and/or a change of the buffer composition.

8. The method of claim 1 or 2, including at least one step of virus inactivation.

9. The method of claim 8, wherein the step of virus inactivation comprises treatment of the plasma or of the fraction containing anti-D IgG with a detergent and tri(n-butyl) phosphate, the phases of the mixture containing solvent and detergent being separated and the clear lower phase being used.

10. The method of claim 8, wherein the step of virus inactivation comprises heat treatment.

11. The method of claim 1 or 2, including at least one step of virus removal.

12. The method of claim 11, wherein the step of virus removal comprises nanofiltration.

13. The method of claim 1 or 2, wherein the starting plasma or the statement plasma fraction prior to the ion exchange chromatography step in stage (a) is subjected to at least one of the following steps:
   a) freezing the plasma, the cryoprecipitate being separated by filtration and/or centrifugation after thawing and before further use,
   b) treatment with a solvent-detergent-mixture incubation at approximately 37° C. and phase separation.

14. A pharmaceutical preparation comprising a preparation with a specific activity of more than 2% anti-D IgG per gram total IgG produced according to the method of claim 1, in combination with a pharmaceutically acceptable carrier or additive.

15. The pharmaceutical preparation of claim 14 wherein the preparation comprises 20–200 µg/ml anti-D IgG, less than 5 µg/ml IgA, the entire protein content being at most 10%, the pH value lying between 5.0 and 7.5, and the slightly hypertonic osmolarity being adjusted by a combination of glycine or sugar and NaCl.

16. The method of claim 7, wherein the elution in step (b) is carried out by changing the ionic concentration or the conductivity of the composition.

17. A pharmaceutical preparation comprising a preparation produced according to the method of claim 13, in combination with a pharmaceutically acceptable carrier or additive.

18. The pharmaceutical preparation of claim 17 wherein the preparation comprises 20–200 µg/ml anti-D IgG, less than 5 µg/ml IgA, the entire protein content being at most 10%, the pH value lying between 5.0 and 7.5, and the slightly hypertonic osmolarity being adjusted by a combination of glycine or sugar and NaCl.

19. The method of claim 13, wherein the pH value lies between 5.0 and 5.5.

20. The method of claim 15, wherein the pH value lies between 5.0 and 5.5.

* * * * *

UNITED STATES PATENT AND TRADEMARK OFFICE
CERTIFICATE OF CORRECTION

PATENT NO.      :   5,593,675
DATED           :   January 14, 1997
INVENTOR(S)     :   Gerhard Hodler; Peter Lerch; Martin Stucki It is certified that error appears in the above identified patent and that said Letters Patent is hereby corrected as shown below:

In column 8, claim 2, line 34, please delete "steps (a) and (a)" and substitute therefore -- steps (a) and (b) --.

Signed and Sealed this

Twenty-second Day of April, 1997

*Attest:*

BRUCE LEHMAN

*Commissioner of Patents and Trademarks*

*Attesting Officer*

UNITED STATES PATENT AND TRADEMARK OFFICE
CERTIFICATE OF CORRECTION

PATENT NO. : 5,593,675
DATED : January 14, 1997
INVENTOR(S) : Gerhard Hodler, et. al.

It is certified that error appears in the above-indentified patent and that said Letters Patent is hereby corrected as shown below:

In column 8, claim 2, line 34, please delete "in-that" and substitute therefore --in that--.

In column 8, claim 4, line 44, please delete "adsorbant" and substitute therefore --adsorbent--.

In column 9, claim 13, line 4, please delete "statement" and substitute therefore --starting--.

In column 9, claim 13, line 5, please delete "stage" and substitute therefore --step--.

In column 9, claim 13, line 10, please delete "solvent-detergent-mixture incubation" and substitute therefore --solvent-detergent-mixture, incubation--.

In column 9, claim 13, line 11, please delete the "C." and substitute therefore --C--.

Signed and Sealed this

First Day of July, 1997

Attest:

*Attesting Officer*

BRUCE LEHMAN

*Commissioner of Patents and Trademarks*